(12) United States Patent
Sako et al.

(10) Patent No.: US 8,975,713 B2
(45) Date of Patent: Mar. 10, 2015

(54) ULTASOUND PROBE PROVIDING DUAL BACKING LAYER

(75) Inventors: Akifumi Sako, Tokyo (JP); Tomoko Takenaka, Tokyo (JP); Kazunari Ishida, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/976,758

(22) PCT Filed: Jan. 5, 2012

(86) PCT No.: PCT/JP2012/000047
§ 371 (c)(1),
(2), (4) Date: Jun. 27, 2013

(87) PCT Pub. No.: WO2012/093662
PCT Pub. Date: Jul. 12, 2012

(65) Prior Publication Data
US 2013/0285174 A1    Oct. 31, 2013

(30) Foreign Application Priority Data

Jan. 6, 2011 (JP) .................................. 2011-001485

(51) Int. Cl.
*A61B 8/14* (2006.01)
*A61B 8/00* (2006.01)
(Continued)

(52) U.S. Cl.
CPC .............. *H01L 29/84* (2013.01); *B06B 1/0292* (2013.01); *G10K 11/002* (2013.01); *A61B 8/4444* (2013.01)
USPC ........... 257/416; 600/437; 600/462; 600/459; 29/594; 257/E21.481; 438/48

(58) Field of Classification Search
USPC .......... 65/396, 29.18; 73/1.82, 703, 632, 633; 128/200.16; 156/73.1, 73.3, 580.1, 156/580.2; 257/E21.481, E21.484, 257/E21.518, 416; 324/754.25; 340/943; 433/86, 119; 600/407, 437, 467, 462, 600/459; 601/2, 22; 702/39, 159, 171; 310/327, 334, 335; 29/594; 438/48, 438/421, 422, 456, 42, 43
See application file for complete search history.

(56) References Cited

U.S. PATENT DOCUMENTS 5,457,863 A * 10/1995 Thomas et al. ............... 29/25.35
6,467,138 B1 * 10/2002 Aime ........................... 29/25.35
(Continued)

FOREIGN PATENT DOCUMENTS

| JP | 2004-188203 | 7/2004 |
| JP | 2007-158468 | 6/2007 |
| WO | 2010-122982 | 10/2010 |

OTHER PUBLICATIONS

Vepa, Ranjan. "Dynamics of Smart Structures." 2010. John Wiley & Sons. 226-227.*
(Continued)

*Primary Examiner* — Evan Pert
*Assistant Examiner* — Gustavo Ramallo
(74) *Attorney, Agent, or Firm* — Brundidge & Stanger, P.C.

(57) ABSTRACT

Disclosed is an ultrasonic probe comprising: CMUT cells (13) that mutually convert ultrasonic waves and electrical signals; a semiconductor substrate (15) that has a plurality of the CMUT cells (13) formed on the surface thereof; an acoustic lens (3) that is provided on the front face side of the CMUT cells (13); and a backing layer (5) that is provided on the rear face side of the semiconductor substrate (15). The backing layer (5) is formed by a first backing layer (27) that makes contact with the semiconductor substrate, and a second backing layer (29) that is provided on the rear face side of the backing layer (27). The acoustic impedance of the backing layer (27) is set based on the sheet thickness of the semiconductor substrate (15). The backing layer (29) is formed by attenuating material capable of attenuating ultrasonic waves transmitted through the backing layer (27). Multiple reflection of reflection echoes is suppressed by setting the acoustic impedance of the backing layer (29) to match the acoustic impedance of the backing layer (27).

12 Claims, 13 Drawing Sheets

(51) Int. Cl.
*H04R 31/00* (2006.01)
*H01L 21/00* (2006.01)
*H01L 29/84* (2006.01)
*B06B 1/02* (2006.01)
*G10K 11/00* (2006.01)

(56) References Cited

U.S. PATENT DOCUMENTS

| | | | |
|---|---|---|---|
| 6,761,692 B2* | 7/2004 | Angelsen et al. | 600/459 |
| 7,230,368 B2* | 6/2007 | Lukacs et al. | 310/335 |
| 7,790,490 B2* | 9/2010 | Caliano et al. | 438/48 |
| 7,830,069 B2* | 11/2010 | Lukacs et al. | 310/334 |
| 8,408,063 B2* | 4/2013 | Sano et al. | 73/632 |
| 8,773,002 B2* | 7/2014 | Jin et al. | 310/334 |
| 2010/0242612 A1* | 9/2010 | Sano et al. | 73/632 |
| 2011/0034809 A1* | 2/2011 | Eberle et al. | 600/467 |
| 2011/0071396 A1* | 3/2011 | Sano et al. | 600/443 |
| 2011/0178407 A1* | 7/2011 | Lu et al. | 600/459 |

OTHER PUBLICATIONS

International Search Report from International Application No. PCT/JP2012/000047 mailed Mar. 6, 2012.

* cited by examiner (a) Thickness of substrate =5um (b) Thickness of substrate =25um (c) Thickness of substrate =50um (d) Thickness of substrate =200um (a)

(b)

ULTASOUND PROBE PROVIDING DUAL BACKING LAYER

TECHNICAL FIELD

The present invention relates to an ultrasound probe and, more particularly, to an ultrasound probe that mutually converts ultrasound and an electric signal using capacitive vibration elements.

BACKGROUND ART

In an ultrasonic diagnostic apparatus that transmits ultrasound to a subject and receives a reflected wave of the ultrasound to obtain an image, an ultrasound probe that transmits and receives the ultrasound between the ultrasound probe and the subject is used. It is known that, in the ultrasound probe, an acoustic lens that comes into contact with the subject, a transducer that mutually converts the ultrasound and an electric signal, and a backing layer that absorbs the ultrasound radiated on the rear face side of the transducer are provided.

As such a transducer, CMUT (Capacitive Micromachined Ultrasonic Transducers) is described in Non Patent Literature 1. The CMUT is formed by patterning a large number of CMUT cells (hereinafter referred to as capacitive vibration elements as appropriate.) on a semiconductor substrate using a lithography technique. The CMUT cells have a structure in which a recess is formed in an insulating layer formed on a semiconductor substrate, an opening of the recess is closed by a membrane to form a vacuum (or gas-filled) gap, and a pair of electrodes are provided to be opposed to each other on the front face of the membrane and the rear face of the insulating layer across the vacuum gap. The CMUT cells apply an electric signal having an ultrasonic frequency between the pair of electrodes to thereby vibrate the membrane and transmit the ultrasound to the inside of the subject. The CMUT cells receive, in the membrane, reflection echoes from the inside of the subject and convert displacement of the membrane into an electric signal as a change in capacitance between the pair of electrodes. The plurality of CMUT cells are separated from one another by a frame body composed of an insulating layer. One oscillator is formed by an aggregate of the plurality of CMUT cells having such a structure. A plurality of such oscillators are one-dimensionally or two-dimensionally arrayed on the same semiconductor substrate to form an ultrasound probe. The CMUT has advantages that, for example, a frequency band of usable ultrasound is wide and sensitivity is high compared with a transducer made of piezoelectric ceramic.

On the other hand, the CMUT can increase and decrease an electromechanical coupling factor by applying a direct-current bias between the electrodes and increasing and decreasing the direct-current bias voltage. However, in order to increase the sound pressure of the ultrasound, it is necessary to reduce the electromechanical coupling factor. Therefore, when it is attempted to obtain desired sound pressure, efficiency of conversion of the ultrasound into the electric signal is deteriorated. Therefore, in general, the CMUT has low conversion efficiency of the ultrasound compared with the transducer made of the piezoelectric ceramic. When the conversion efficiency is low, the reflection echoes from the subject are not converted into an electric signal and are transmitted through the semiconductor substrate to reach an interface of the backing layer and are reflected. As a result, a problem of multiple reflection in which the reflection echoes are repeatedly reflected between the subject and the interface of the backing layer occurs. In order to suppress such multiple reflection, Patent Literature 1 proposes to match acoustic impedances of the semiconductor substrate and the backing layer.

CITATION LIST

Patent Literature

Patent Literature 1: U.S. Pat. No. 6,831,394

Non Patent Literature

Non Patent Literature 1: Development of Ultrasonic Transducer "Mappie" with cMUT Technology, MEDIX, Hitachi Medical Corporation, 2009, vol. 51, pp 31-34

SUMMARY OF INVENTION

Technical Problem

However, Patent Literature 1 does not take into account the fact that a suppression effect for the multiple reflection is different depending on the thickness of the semiconductor substrate even if the acoustic impedance of the backing layer is set to match the acoustic impedance of the semiconductor substrate.

A problem to be solved by the present invention is to suppress the multiple reflection of the reflection echoes while taking into account the thickness of the semiconductor substrate in the ultrasound probe in which the CMUT is used.

Solution to Problem

In order to solve the problem, an ultrasound probe according to the present invention is an ultrasound probe including: a capacitive vibration element configured to mutually convert ultrasound and an electric signal; a semiconductor substrate including a plurality of the capacitive vibration elements formed on the surface thereof; an acoustic lens provided on the front face side of the capacitive vibration element; and a backing layer provided on the rear face side of the semiconductor substrate, wherein the backing layer includes a first backing layer set in contact with the semiconductor substrate and a second backing layer provided on the rear face side of the first backing layer, the acoustic impedance of the first backing layer is set on the basis of the thickness of the semiconductor substrate, the second backing layer is formed of an attenuating material capable of attenuating the ultrasound transmitted through the first backing layer, and the acoustic impedance of the second backing layer is set to match the acoustic impedance of the first backing layer.

In this case, the acoustic impedance of the first backing layer can be set to a value close to the acoustic impedance of the acoustic lens compared with the acoustic impedance of the semiconductor substrate.

The first backing layer can be formed by mixing, in resin, an adjusting material for adjusting a coefficient of linear expansion of the first backing layer to be close to a coefficient of linear expansion of the semiconductor substrate. As the adjusting material, for example, carbon fiber or glass fiber can be used. The adjusting material can be mixed in the resin with the longitudinal direction of the fiber adjusted to the longitudinal direction of the first backing layer.

The first backing layer can be formed by filing resin in porous ceramic.

Advantageous Effects of Invention

According to the present invention, it is possible to suppress the multiple reflection of the reflection echoes while taking into account the thickness of the semiconductor substrate in the ultrasound probe in which the CMUT is used.

DESCRIPTION OF EMBODIMENTS

Figure 1:
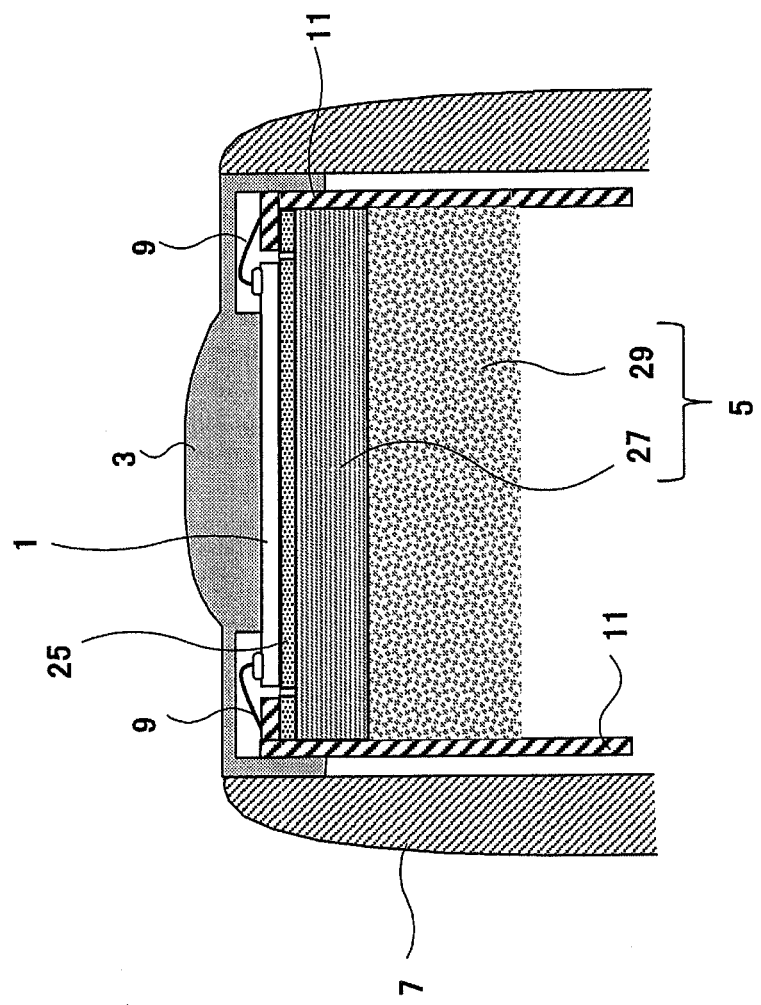
FIG. 1 is a sectional view in the minor axis direction of an ultrasound probe according to an embodiment of the present invention.
Figure 2:
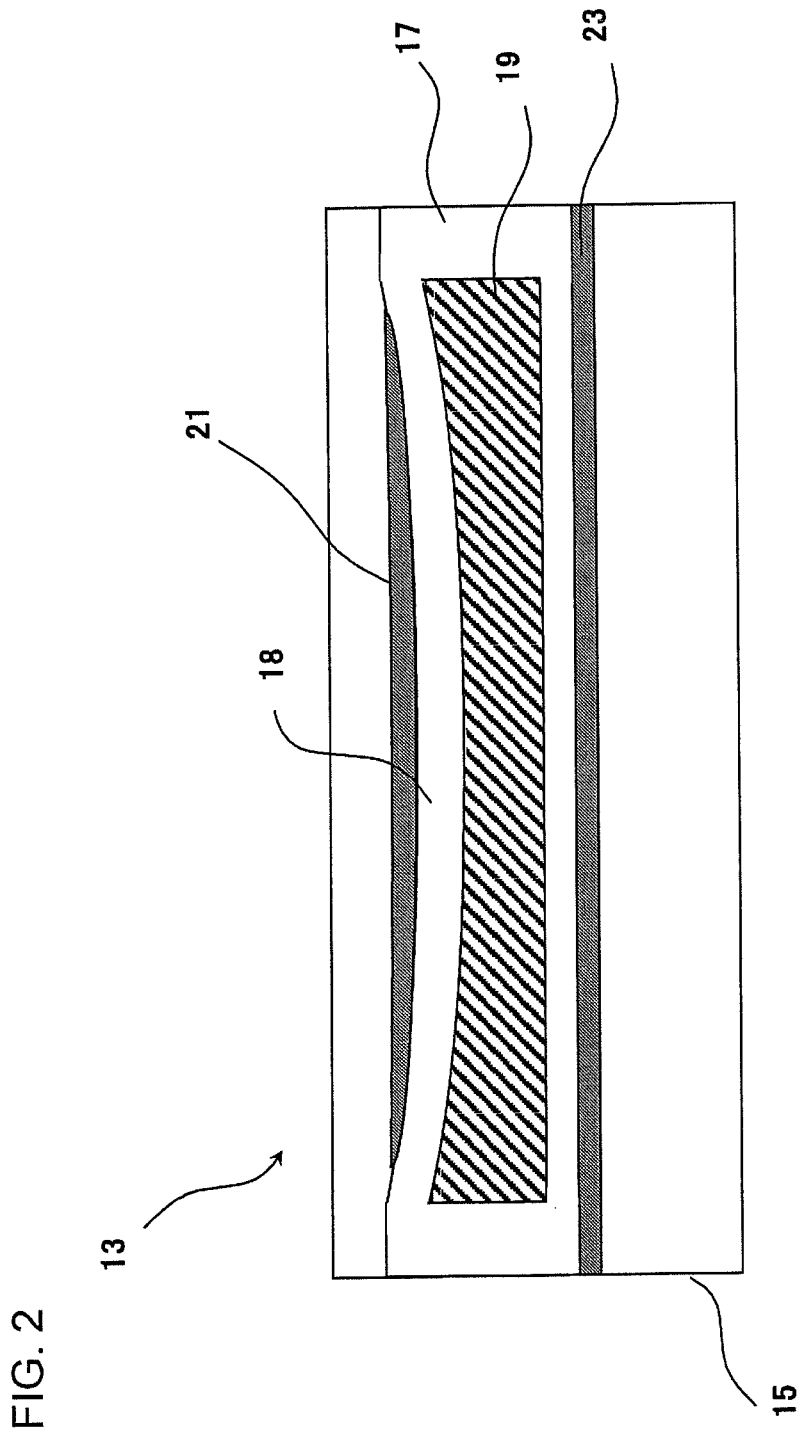
FIG. 2 is a schematic diagram of a cross section of a CMUT cell.
Figure 3:
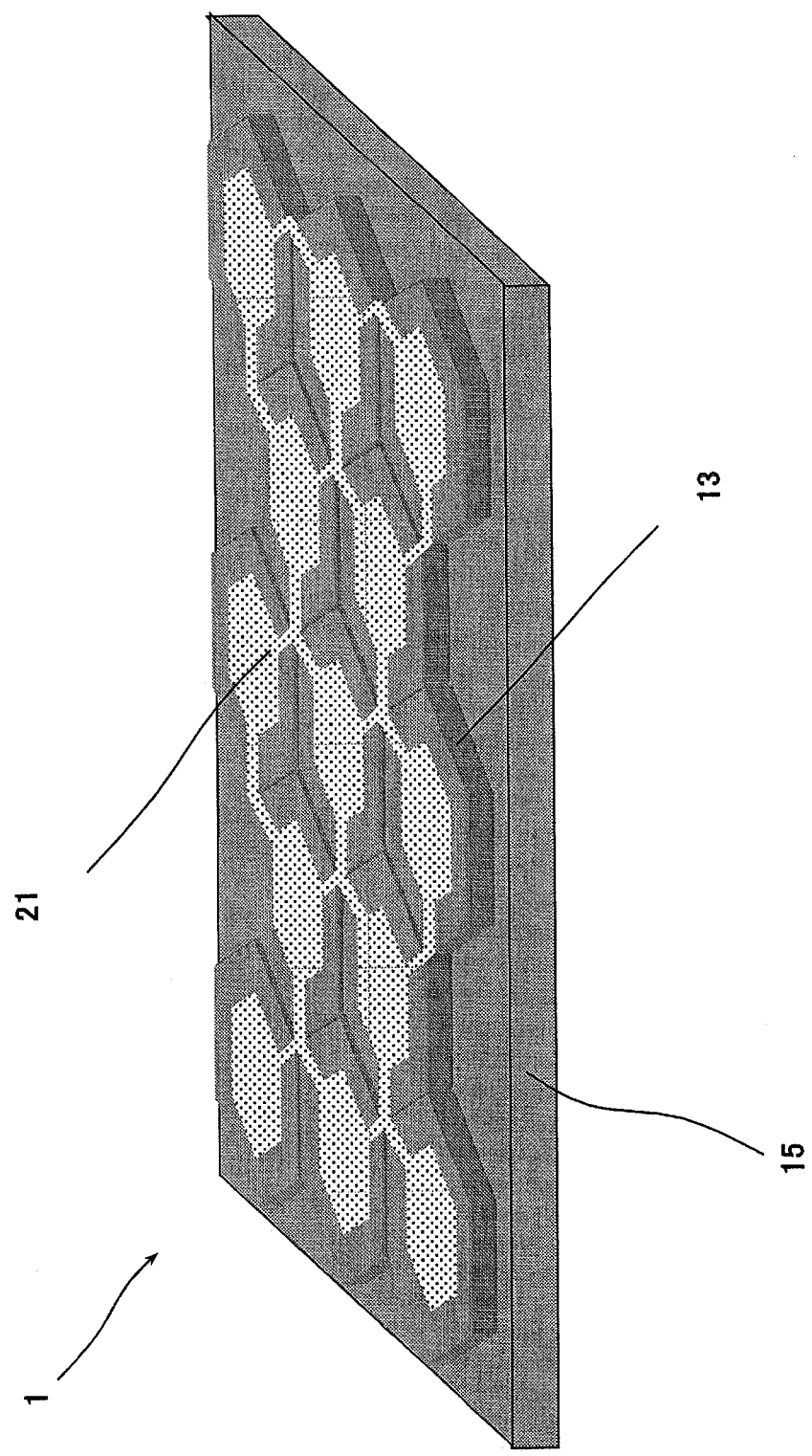
FIG. 3 is a perspective view of a CMUT chip.

The present invention is explained below on the basis of an embodiment.
Embodiment As shown in FIGS. 1 to 3, an ultrasound probe according to this embodiment is formed by attaching, to a case 7, a CMUT chip 1 formed by a CMUT cell 13, which is a capacitive vibration element, and a semiconductor substrate 15 including a large number of CMUT cells 13 formed on the surface thereof, an acoustic lens 3 provided on the front face side of the CMUT chip 1, and a backing layer 5 provided on the rear face side of the CMUT chip 1. A flexible substrate 11 is connected to the CMUT chip 1 via a metal wire 9. The flexible substrate 11 is connected to a not-shown external device such as a power supply via an electric wire. Consequently, it is possible to transmit a driving signal to the CMUT chip 1 and apply a direct-current bias voltage to the CMUT chip 1. Further, it is possible to convert reflection echoes received by the CMUT chip 1 into an electric signal and transmit the electric signal to the external device.

As shown in FIG. 2, each of the CMUT cells 13 has a structure including a vacuum (or gas-filled) gap 19 formed by closing, with a membrane 18, an opening of a recess formed in an insulating layer 17 made of an insulating material, a pair of electrodes 21 and 23 being provided on the front face of the membrane 18 and the rear face of the insulating layer 17 across the vacuum gap 19. The CMUT cell 13 applies an electric signal having an ultrasonic frequency between the pair of electrodes 21 and 23 to thereby vibrate the membrane 18 with an electrostatic force and transmit ultrasound to the inside of a subject. The CMUT cell 13 receives reflection echoes from the inside of the subject in the membrane 18 and converts displacement of the membrane 18 into an electric signal as a change in capacitance between the pair of electrodes 21 and 23. Each of the CMUT cells 13 is separated by a frame body formed by the insulating layer 17. As shown in FIG. 3, each of the CMUT cells 13 is patterned and formed on the semiconductor substrate 15 by a semiconductor manufacturing technique such as a lithography technique. One oscillator is formed by an aggregate of a large number of the CMUT cells 13 having such a structure. The CMUT chip 1 is formed by one-dimensionally or two-dimensionally arraying a plurality of such oscillators on the same semiconductor substrate 15. Note that, for example, one oscillator is formed by a plurality of the aggregates of a large number of CMUT cells 13 having such a structure one-dimensionally or two-dimensionally arranged on the semiconductor substrate 15 while being patterned by a manufacturing technique for a conductor device. Note that the semiconductor substrate 15 is formed of, for example, silicon.

As shown in FIG. 1, the acoustic lens 3 that focuses ultrasound irradiated from the CMUT chip 1 is attached to the front face side of the CMUT chip 1. The acoustic lens 3 is a convex acoustic lens including a convex portion projecting in an irradiating direction of the ultrasound. The acoustic lens 3 is formed of a material having an acoustic impedance close to the acoustic impedance of the subject. For example, when a living organism is the subject, the acoustic lens 3 is formed of a material having an acoustic impedance close to 1.5 MRayl, which is the acoustic impedance of the living organism.

The backing layer 5 that absorbs ultrasound to the back of the CMUT chip 1 is provided on the rear face side of the CMUT chip 1. The backing layer 5 and the semiconductor substrate 15 of the CMUT chip 1 adhere via an adhesive layer 25. The thickness of the adhesive layer 25 is set smaller than wavelength in the working frequency of ultrasound in use. For example, it is desirable to set the thickness of the adhesive layer 25 to 10 μm or less. Consequently, since most of the ultrasound having the working frequency is transmitted through the adhesive layer 25, it is possible to neglect the influence of the acoustic impedance of the adhesive layer 25.

Next, a characteristic configuration of this embodiment is explained. As shown in FIG. 1, the backing layer 5 includes a first backing layer 27 set in contact with the semiconductor substrate 15 via the adhesive layer 25 and a second backing layer 29 provided on the rear face side of the first backing layer. The backing layer 27 is formed of a material having an acoustic impedance of a set value set on the basis of the thickness of the semiconductor substrate 15. The backing layer 29 is formed of a material having an attenuation ratio of ultrasound higher than that of the backing layer 27 and having an acoustic impedance close to the acoustic impedance of the backing layer 27.

The operation of the ultrasound probe according to this embodiment formed in this way is explained. A predetermined direct-current bias voltage is applied between the electrodes 21 and 23 of the CMUT cell 13 from the external device via the flexible substrate 11. An electromechanical coupling factor of the CMUT cell 13 is set to a predetermined value. When a predetermined driving signal is transmitted to between the electrodes 21 and 23 from the external device via the flexible substrate 11, ultrasound is generated according to the electromechanical coupling factor. The generated ultrasound is focused by the acoustic lens 3 and irradiated on the subject. Reflection echoes of the ultrasound reflected on the subject passes through the acoustic lens 3 and vibrates the membrane 18 of the CMUT cell 13. The capacitance of the vacuum gap 19 is changed by this vibration. An electric signal corresponding to this change is output from between the electrodes 21 and 23. This electric signal is transmitted from the CMUT chip 1 to the external device via the flexible substrate 11 and processed as appropriate to generate an ultrasonic image.

Figure 4:
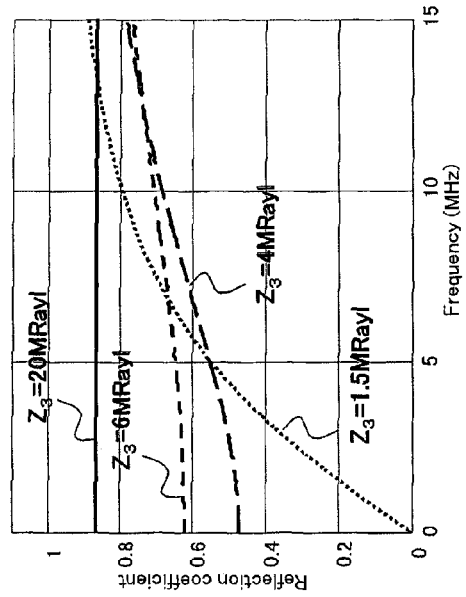
FIG. 4 is a graph showing a relation between the sound pressure reflection coefficient of an interface between a semiconductor substrate and a backing layer and the thickness of the semiconductor layer.
Figure 4:
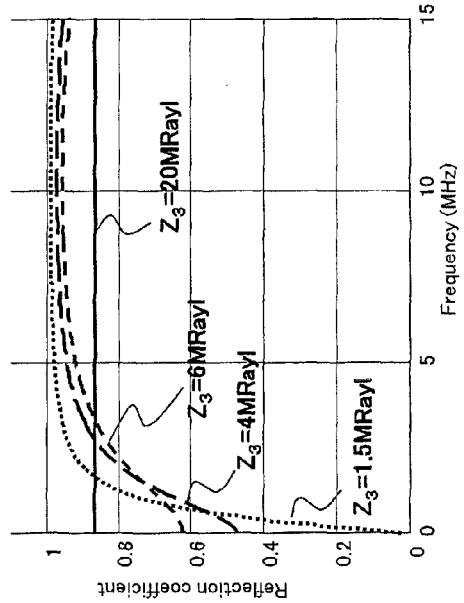
Figure 4:
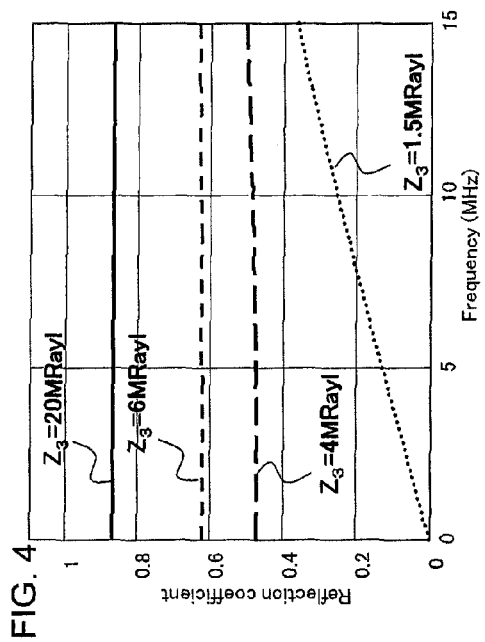
Figure 4:
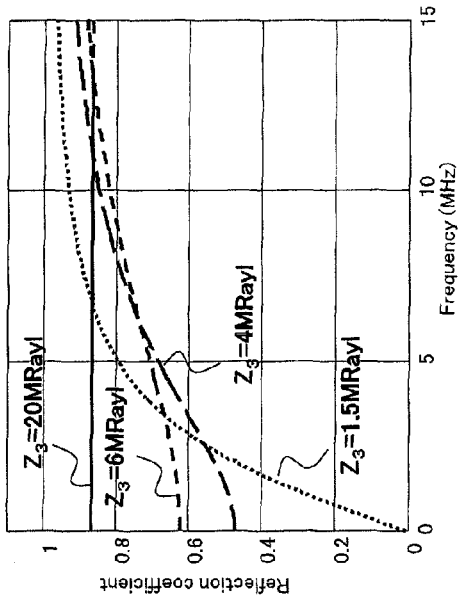

Next, a characteristic operation of the ultrasound probe according to this embodiment is explained. In order to obtain predetermined sound pressure, the electromechanical coupling factor of the CMUT cell 13 is set small. Therefore, compared with a transducer made of piezoelectric ceramic, the CMUT has low efficiency of converting ultrasound into an electric signal. Reflection echoes not converted into the electric signal are transmitted through the semiconductor substrate 15. When the reflection echoes are reflected on an interface between the semiconductor substrate 15 and the backing layer 5, multiple reflection is caused. In this case, when the thickness of the semiconductor substrate 15 is large, for example, the thickness is 200 μm, if the acoustic impedances of the semiconductor substrate 15 and the backing layer 5 are matched, the sound pressure reflection coefficient of the interface between the semiconductor substrate 15 and the backing layer 5 can be reduced. However, if the thickness of the semiconductor substrate 15 is set smaller than 200 μm, the sound pressure reflection coefficient of the interface between the semiconductor substrate 15 and the backing layer 5 increases. For example, according to FIG. 4 referred to below, when the thickness of the semiconductor substrate 15 is 5 μm, 25 μm, and 50 μm, the sound pressure reflection coefficient of the interface between the semiconductor substrate 15 and the backing layer 5 can be reduce if the acoustic impedance of the backing layer 5 is set lower than the acoustic impedance (20 MRayl) of the semiconductor substrate 15. This is surmised to be because, if the thickness of the semiconductor substrate 15 is sufficiently small compared with the wavelength of ultrasound in use, for example, 1/20 or less of the wavelength of the ultrasound in use, the influence of the acoustic impedance of the semiconductor substrate 15 can be neglected. Therefore, since the interface between the semiconductor substrate 15 and the backing layer 5 can be regarded as an interface between the acoustic lens 3 and the backing layer 5, it is possible to reduce the sound pressure reflection coefficient of the interface between the semiconductor substrate 15 and the backing layer 5 by reducing the acoustic impedance of the backing layer 5 to be close to the acoustic impedance (1.5 MRayl) of the acoustic lens 3. Therefore, since the reflection echoes transmitted through the semiconductor substrate 15 is transmitted through the interface between the semiconductor substrate 15 and the backing layer 5, it is possible to suppress multiple reflection in which the reflection echoes are repeatedly reflected between this interface and the subject. If the thickness of the semiconductor substrate 15 is reduced, the sound pressure reflection coefficient of the interface between the semiconductor substrate 15 and the backing layer 5 tends to decrease. Therefore, it is desirable to reduce the thickness of the semiconductor substrate 15. On the other hand, if the thickness of the semiconductor substrate 15 is reduced, a problem such as deterioration in the strength of the semiconductor substrate 15 occurs. Therefore, the thickness of the semiconductor substrate 15 is desirably equal to or larger than 25 μm and, more desirably equal to or larger than 25 μm and equal to or smaller than 50 μm.

Incidentally, in order to reduce the acoustic impedance of the backing layer 5, thermoplastic resin such as 6-Nylon is used for the material of the backing layer 5. In general, such resin has a large coefficient of linear expansion. On the other hand, the semiconductor substrate 15 is formed of silicon or the like having a small coefficient of linear expansion. Therefore, structural distortion such as a warp is caused in a joined body of the semiconductor substrate 15 and the backing layer 5 by thermal stress in bonding the semiconductor substrate 15 to the backing layer 5. In particular, deformation is large and the structural distortion is large in the longitudinal direction of the backing layer 5. When the structural distortion occurs in this way, a target dimension is not obtained and the reliability of the apparatus is deteriorated. Therefore, in this embodiment, the first backing layer 27 having a coefficient of linear expansion reduced to be close to that of the semiconductor substrate 15 is arranged on a side in contact with the semiconductor substrate 15. For example, a carbon fiber or glass fiber is mixed in resin to form the backing layer 27 such that the longitudinal direction of the fiber extends along the longitudinal direction of the backing layer 27.

On the other hand, the backing layer 27 having the reduced coefficient of linear expansion has a low attenuation ratio of ultrasound. The backing layer 27 alone cannot fully attenuate the ultrasound. Therefore, in this embodiment, the second backing layer 29 having an attenuation ratio of ultrasound higher than that of the backing layer 27 is arranged on the rear face side of the backing layer 27. As the material of the backing layer 29, resin having an attenuation ratio of ultrasound higher than that of the backing layer 27 and having a modulus of elasticity smaller than that of the resin used for the backing layer 27, for example, polyurethane, epoxy resin, ferrite rubber, or the like can be used. If a difference between the acoustic impedances of the backing layer 27 and the backing layer 29 is large, the sound pressure reflection coefficient of the interface between the backing layer 27 and the backing layer 29 increases. Therefore, tungsten, silicon, or the like is mixed in the resin forming the backing layer 29 to set the acoustic impedance of the backing layer 29 close to the acoustic impedance of the backing layer 27. Consequently, since the sound pressure reflection coefficient of the interface between the backing layer 27 and the backing layer 29 can be reduced, the reflection echoes can be attenuated by the backing layer 29 having a high attenuation ratio. Details of the first backing layer 27 and the second backing layer 29 are explained below on the basis of examples.

EXAMPLE 1

The inventors of the present invention learned that, even if the acoustic impedances of the semiconductor substrate and the backing layer are matched, a degree of suppression of multiple reflection is low if the thickness of the semiconductor substrate is small. The principle of the present invention based on the fact that it is effective for suppression of multiple reflection to change the acoustic impedance of the backing layer according to the thickness of the semiconductor substrate is explained.

Reflection echoes from the subject is transmitted through the semiconductor substrate, reflected on the interface between the semiconductor substrate and the backing layer, and repeatedly reflected between this interface and the subject, whereby multiple reflection occurs. Therefore, if the reflectivity of ultrasound (the sound pressure reflection coefficient) of the interface between the semiconductor substrate and the backing layer can be reduced, it is possible to suppress multiple reflection. The coefficient of reflection (mr) can be calculated by Formula 1 below.

$$mr = \frac{\left(\frac{Z_1 - Z_2}{Z_1 + Z_2}\right) + \left(\frac{Z_3 - Z_1}{Z_3 + Z_1}\right)e^{-2\gamma_1 d_1}}{1 + \left(\frac{Z_1 - Z_2}{Z_1 + Z_2}\right)\left(\frac{Z_3 - Z_1}{Z_3 + Z_1}\right)e^{-2\gamma_1 d_1}} \quad \text{[Formula 1]}$$

mr: sound pressure reflection coefficient of the interface between the semiconductor substrate and the backing layer
$Z_1$: acoustic impedance of the semiconductor substrate
$Z_2$: acoustic impedance of the acoustic lens
$Z_3$: acoustic impedance of the backing layer
$\gamma_1$: propagation constant of the semiconductor substrate
$d_1$: thickness of the semiconductor substrate The sound pressure reflection coefficient (mr) of the interface between the semiconductor substrate and the backing layer was calculated by Formula 1 with the acoustic impedance ($Z_1$) of the semiconductor substrate set to 20 MRayl, the acoustic impedance ($Z_2$) of the acoustic lens set to 1.5 MRayl, the acoustic impedance ($Z_3$) of the backing layer set to 1.5 MRayl, 4 MRayl, 6 MRayl, and 20 MRayl, and the thickness ($d_1$) of the semiconductor substrate set to 5 μm, 25 μm, 50 μm, and 200 μm. Calculated sound pressure reflection coefficients were classified for each of the plate thicknesses of the semiconductor substrate to obtain graphs of FIGS. 4(a) to 4(d). FIG. 4(a) shows the sound pressure reflection coefficient calculated when the thickness of the semiconductor substrate is 5 μm, FIG. 4(b) shows the sound pressure reflection coefficient calculated when the thickness of the semiconductor substrate is 25 μm, FIG. 4(c) shows the sound pressure reflection coefficient calculated when the thickness of the semiconductor substrate is 50 μm, and FIG. 4(d) shows the sound pressure reflection coefficient calculated when the thickness of the semiconductor substrate is 200 μm. FIGS. 4(a) to 4(d) are graphs in which the ordinate indicates the sound pressure reflection coefficient of the interface between the semiconductor substrate and the backing layer and the abscissa indicates the working frequency of ultrasound used for an ultrasonic diagnosis. As the acoustic impedance ($Z_1$) of the semiconductor substrate and the propagation constant ($\gamma_1$) of the semiconductor substrate, the acoustic impedance of silicon, which is a general material of the semiconductor substrate, and the propagation constant of ultrasound were used.

When FIGS. 4(a) to 4(c) in which the thickness of the semiconductor substrate is small and FIG. 4(d) in which the thickness of the semiconductor substrate is large are compared, when the thickness of the semiconductor substrate is small, if the acoustic impedance of the backing layer is set lower than 20 MRayl, which is the acoustic impedance of the semiconductor substrate, it is possible to reduce the sound pressure reflection coefficient of the interface between the semiconductor substrate and the backing layer. On the other hand, when the thickness of the semiconductor substrate is large, if the acoustic impedance of the backing layer is set to 20 MRayl, which is the acoustic impedance of the semiconductor substrate, it is possible to reduce the sound pressure reflection coefficient of the interface between the semiconductor substrate and the backing layer. This is surmised to be because the influence of the acoustic impedance of the semiconductor substrate decreased when the thickness of the semiconductor substrate decreased. That is, since the acoustic lens, the semiconductor substrate, and the backing layer are formed in this order in the ultrasound probe, when the semiconductor substrate is neglected, the interface between the semiconductor substrate and the backing layer can be regarded as the interface between the acoustic lens and the backing layer. Therefore, it is surmised that the sound pressure reflection coefficient on the interface between the semiconductor substrate and the backing layer decreases when the acoustic impedance of the backing layer is reduced to be close that of the acoustic lens.

On the basis of these kinds of knowledge, an example 1 of the ultrasound probe according to the present invention is an ultrasonic prove including, as shown in FIGS. 1 to 3, the CMUT cell 13, which is a capacitive vibration element that mutually converts ultrasound and an electric signal, the semiconductor substrate 15 including a plurality of the capacitive vibration elements formed on the surface thereof, the acoustic lens 3 provided on the front face side of the capacitive vibration element, and the backing layer 5 provided on the rear face side of the semiconductor substrate 15, wherein the backing layer 5 includes the first backing layer 27 set in contact with the semiconductor substrate and the second backing layer 29 provided on the rear face side of the backing layer 27, the acoustic impedance of the first backing layer 27 is set on the basis of the thickness of the semiconductor substrate 15, the second backing layer 29 is formed of an attenuating material that can attenuate the ultrasound transmitted through the first backing layer 27, the acoustic impedance of the second backing layer 29 is set to match the acoustic impedance of the first backing layer 27.

That is, even if the acoustic impedance of the backing layer 5 is the same, since the sound pressure reflection coefficient of the interface between the semiconductor substrate 15 and the backing layer 5 changes according to the thickness of the semiconductor substrate 15, a degree of suppression of multiple reflection changes. Therefore, the acoustic impedance of the first backing layer 27 set in contact with the semiconductor substrate 15 is set to an acoustic impedance effective for suppression of multiple reflection on the basis of the thickness of the semiconductor substrate 15. Consequently, since the degree of suppression of multiple reflection can be improved, it is possible to reduce an unnecessary response due to multiple reflection that causes rendition of a virtual image of an ultrasonic image.

Note that, since the first backing layer 27 is in contact with the semiconductor substrate, a material that can be used for the first backing layer 27 is limited. A material having a high attenuation ratio of ultrasound sometimes cannot be used. Therefore, it is desirable to provide the second backing layer 29 having an attenuation ratio of ultrasound larger than the first backing layer 27 and attenuate reflection echoes transmitted through the first backing layer 25.

Incidentally, according to FIG. 4(b), when the working frequency of ultrasound for the ultrasonic diagnosis is equal to or lower than 5 MHz, if the acoustic impedance of the first backing layer 27 is set to 1.5 MRayl, the sound pressure reflection coefficient of the interface between the semiconductor substrate 15 and the backing layer 27 is the lowest. On the other hand, when the working frequency of ultrasound is 15 MHz, if the acoustic impedance of the first backing layer 27 is set to 6 MRayl, the sound pressure reflection coefficient of the interface between the semiconductor substrate 15 and the backing layer 27 is the lowest. Therefore, it is desirable to set the acoustic impedance of the first backing layer 27 to an acoustic impedance equal to or higher than 1.5 MRayl and equal to or lower than 6 MRayl. In particular, in general, since the working frequency of ultrasound used for the ultrasonic diagnosis is 2 to 15 MHz, when the ultrasound having the working frequency is transmitted by one ultrasound probe, it is possible to improve a degree of suppression of multiple reflection in a wide area of the working frequency by setting the acoustic impedance of the first backing layer 27 to an acoustic impedance equal to or higher than 4 MRayl and equal to or lower than 6 MRayl.

When the thickness of the semiconductor substrate is 50 µm as shown in FIG. 4(c), if the working frequency of ultrasound exceeds 7 MHz, a suppression effect for multiple reflection is lower than in the past when the acoustic impedance of the first backing layer 27 is 1.5 MRayl. Therefore, in this case, it is possible to improve the degree of suppression of multiple reflection in a wide area of the working frequency by setting a set value of the acoustic impedance of the first backing layer 27 to a value exceeding 1.5 MRayl and, desirably, equal to or larger than 4 MRayl and equal to or smaller than 6 MRayl.

Incidentally, in order to set the acoustic impedance of the first backing layer 27 to a small value such as 1.5 MRayl, 4 MRayl, or 6 MRayl, the first backing layer 27 is formed of resin having a low acoustic impedance. Therefore, the coefficient of linear expansion of the first backing layer 27 increases. On the other hand, the semiconductor substrate 15 is formed of silicon or the like having a small coefficient of linear expansion. Therefore, if bonding work for the semiconductor substrate 15 and the first backing layer 27 is performed at high temperature, it is likely that structural distortion is caused by thermal stress that occurs during bonding of the semiconductor substrate 15 and the first backing layer 27.

In this case, it is desirable to set the coefficients of linear expansion of the semiconductor substrate 15 and the first backing layer 27 close to each other. For example, it is desirable to mix carbon fiber, glass fiber, or the like in resin with the longitudinal direction thereof set in the longitudinal direction of the first backing layer and form the first backing layer. It is possible to set the coefficients of linear expansion of the semiconductor substrate 15 and the first backing layer 27 close to each other by filling resin in porous ceramic to form the first backing layer 27.

Figure 5:
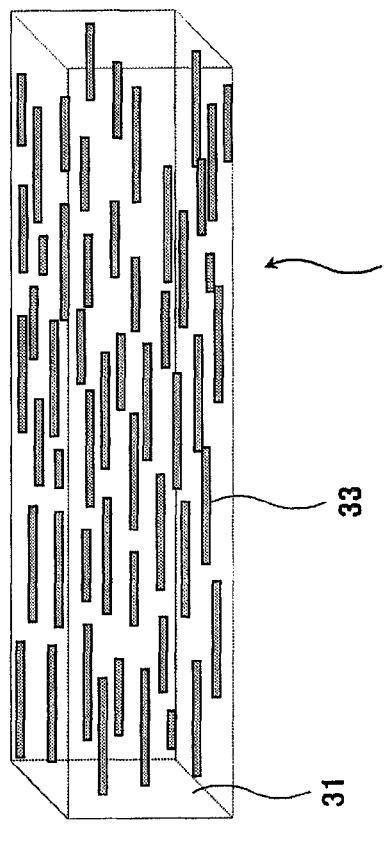
FIG. 5(a) is a conceptual diagram of a first backing layer in an example 1 and FIG. 5(b) is a sectional view in the latitudinal direction of FIG. 5(a).
Figure 5:
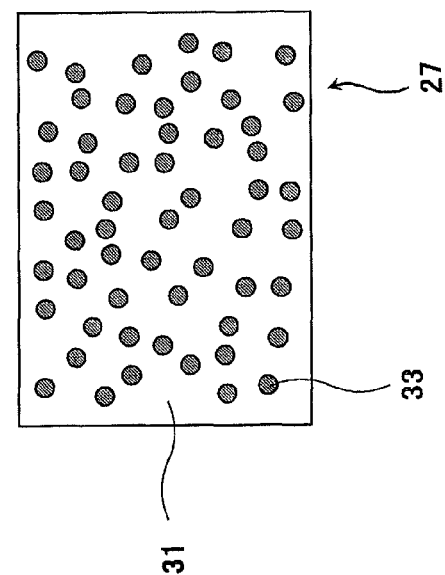

The first backing layer 27 in the example 1 is shown in FIGS. 5(a) and 5(b). In the example 1, 6-Nylon having an acoustic impedance close to that of the acoustic lens 3 is used as a base 31 and carbon fiber 33 is mixed in the base 31 as an adjusting material to form the first backing layer 27. The backing layer 27 can be formed by, for example, injection molding for injecting a mixture of the 6-Nylon and the carbon fiber 33 into a mold. In this case, on the wall surface side of the mold, a flow velocity of the mixture decreases because of friction and the longitudinal direction of the carbon fiber 33 is aligned with an injecting direction. Therefore, the longitudinal direction of the backing layer 27 and the longitudinal direction of the carbon fiber 33 can be aligned by matching the injecting direction of the mixture of the 6-Nylon and the carbon fiber 33 and the longitudinal direction of the backing layer 27. Consequently, the acoustic impedance of the backing layer 27 was set to 4 MRayl and the coefficient of linear expansion in the longitudinal direction of the backing layer 27 was adjusted to 5 ppm/° C. It is possible to set the acoustic impedance and the coefficient of linear expansion of the backing layer 27 to desired values by changing a type of the resin of the base 31 and a type and a mixing amount of the adjusting material as appropriate. The coefficient of linear expansion of silicon, which is the material of the semiconductor substrate 15, is 3 ppm/° C. On the other hand, the coefficient of linear expansion of the 6-Nylon alone is 90 to 100 ppm/° C. and the coefficient of linear expansion of the carbon fiber is about 0 ppm/° C. The backing layer 27 is an anisotropic material having different coefficients of linear expansion in the longitudinal direction and the latitudinal direction.

The backing layer 27 is bonded to the semiconductor substrate 15 on which the CMUT cell 13 is formed. The semiconductor substrate 15 was formed of silicon and formed at thickness of 40 µm. In this state, a mold of the second backing layer 29 was attached to the rear face side of the backing layer 27. The material of the backing layer 29 was poured into the mold to form the backing layer 29 on the rear face side of the backing layer 27. As the material of the backing layer 29, a mixture obtained by using hardening polyurethane as a base and adding tungsten to the base was used. Consequently, the acoustic impedance of the backing layer 29 was set to 4 MRayl and the modulus of elasticity of the backing layer 29 was set to 500 MPa. The thickness of the backing layer 29 was set to 6 mm and the hardening temperature of the backing layer 29 was set to 40° C. The acoustic impedance and the modulus of elasticity of the backing layer 29 can be set to desired values by changing a type of the resin of the base and a type and an adding amount of the additive as appropriate. The thickness of the backing layer 29 can be set as appropriate on the basis of the attenuation ratio of ultrasound of the backing layer 27.

Figure 6:
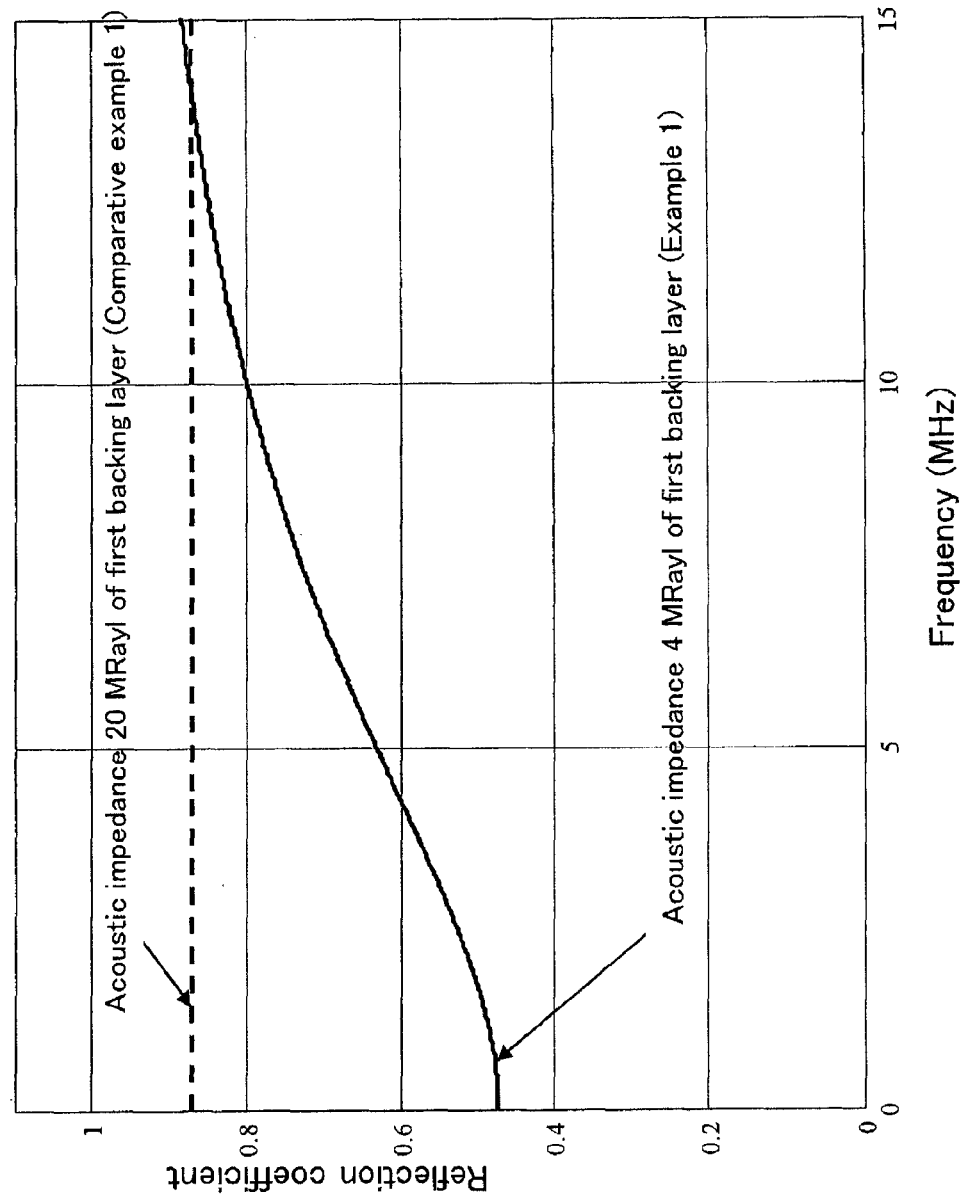
FIG. 6 is a graph showing the sound pressure reflection coefficient of an interface between a semiconductor substrate and a backing layer in the example 1.

The CMUT chip 1 in which the backing layers 27 and 29 are formed is mounted in the case 7 to form the ultrasound probe in the example 1. The sound pressure reflection coefficient of ultrasound on the interface between the semiconductor substrate 15 and the backing layer 27 of this ultrasound probe is shown in FIG. 6. FIG. 6 is a graph in which the ordinate indicates the sound pressure reflection coefficient of the interface between the semiconductor substrate 15 and the backing layer 27 and the abscissa indicates the working frequency of ultrasound used for an ultrasonic diagnosis. An ultrasound probe in which, in order to match the acoustic impedance of the backing layer 27 to the acoustic impedance of the semiconductor substrate, the acoustic impedance was set to 20 MRayl using a composite material of PVC-tungsten and the other components are the same as those in the example 1 is described in FIG. 6 as a comparative example 1.

As it is evident from FIG. 6, the sound pressure reflection coefficient on the interface between the semiconductor substrate 15 and the backing layer 27 is lower at the general working frequency of ultrasound (2 to 15 MHz) in the example 1 in which the acoustic impedance of the backing layer 27 is set close to the acoustic impedance of the acoustic lens 3 than in the comparative example 1 in which the acoustic impedance of the backing layer 27 is matched to the acoustic impedance of the semiconductor substrate 15. For example, when the working frequency of ultrasound was 5 MHz, the sound pressure reflection coefficient was 85% in the comparative example 1. However, in the example 1, the sound pressure reflection coefficient was able to be reduced to 63%. That is, since the ultrasound probe in the example 1 has a high degree of suppression of multiple reflection, it is possible to suppress a virtual image due to multiple reflection from appearing in an ultrasonic image and obtain a highly reliable ultrasonic image.

Figure 7:
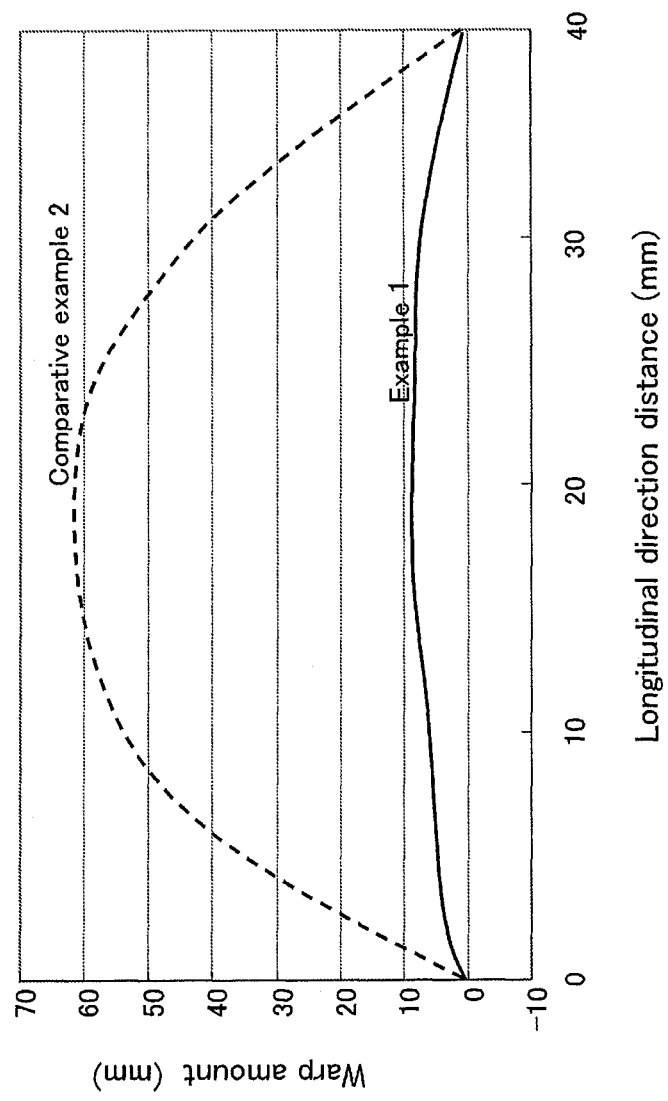
FIG. 7 is a graph showing a warp amount of a bonded body for the semiconductor substrate and the backing layer in the example 1.

On the other hand, a warp is caused in a bonded body of the semiconductor substrate 15 and the backing layer 27 by heating during the bonding of the semiconductor substrate 15 and the backing layer 27. An amount of the warp is shown in FIG. 7. FIG. 7 is a graph in which the ordinate indicates the warp amount of the bonded body and the abscissa indicates a distance in the longitudinal direction of the backing layer. A backing layer having a coefficient of linear expansion of 60 ppm/° C. formed using a mixed material of nylon and tungsten is described in FIG. 7 as a comparative example 2. According to FIG. 7, although a warp of about 70 mm occurs in the comparative example 2, the warp amount can be reduced to about 10 mm in the example 1. Therefore, it is possible to reduce structural distortion due to a warp and improve accuracy and reliability of the ultrasound probe.

Note that, the coefficient of linear expansion of the second backing layer 29 was 100 ppm/° C. However, when a material having a modulus of elasticity smaller than that of the first backing layer 27 and hardening temperature lower than that of the first backing layer 27 is used for the second backing layer 29, thermal stress that occurs between the backing layers 27 and 29 can be absorbed by the backing layer 29. Consequently, it is possible to suppress structural distortion between the backing layers 27 and 29.

Note that a mixing amount of the carbon fiber 33 of the first backing layer 27 can be set to, for example 40 vol %. However, if the carbon fiber 33 increases, the carbon fiber 33 in the cross section of the backing layer 27 increases and the acoustic impedance increases. Therefore, it is desirable to set an upper limit of the mixing amount of the carbon fiber 33 to an amount equal to or smaller than 50 vol %. The length of the carbon fiber 33 can be selected as appropriate. However, for example, the carbon fiber 33 having length of 3 mm can be used.

In the example 1, the coefficient of linear expansion of the backing layer 27 is adjusted by the carbon fiber 33. However, the coefficient of linear expansion can be adjusted by glass fiber instead of the carbon fiber 33.

Further, the acoustic impedance of the backing layer 27 can be adjusted by mixing silica or tungsten in the backing layer 27.

EXAMPLE 2

Figure 8:
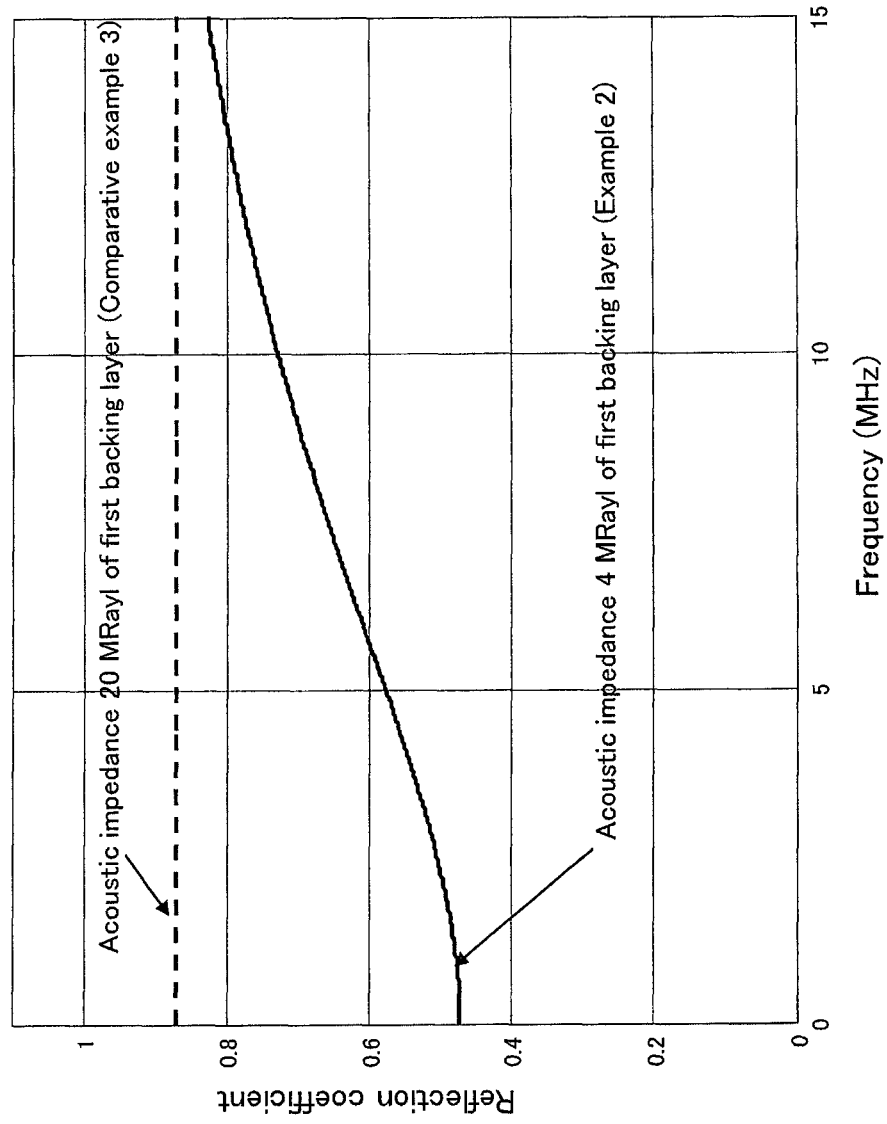
FIG. 8 is a graph showing the sound pressure reflection coefficient of an interface between a semiconductor substrate and a backing layer in an example 2.

The sound pressure reflection coefficient of ultrasound on the interface between the semiconductor substrate 15 and the backing layer 27 of an ultrasound probe in an example 2 is shown in FIG. 8. The example 2 is different from the example 1 in that the thickness of the semiconductor substrate 15 is set to 30 µm. Further, the example 2 is different from the example 1 in that the second backing layer 29 is formed of a mixed material of epoxy resin and tungsten. Since the other components are the same as those in the example 1, explanation of the components is omitted. In the backing layer 29 in the example 2, an acoustic impedance is set to 4 MRayl, a modulus of elasticity is set to 500 MPa, thickness is set to 6 mm, a coefficient of linear expansion is set to 100 ppm/° C., and hardening temperature is set to 40° C. That is, the backing layer 29 in the example 2 is the same as that in the example 1 except a composition.

FIG. 8 is a graph in which the ordinate indicates the sound pressure reflection coefficient of the interface between the semiconductor substrate 15 and the backing layer 27 and the abscissa indicates the working frequency of ultrasound used for an ultrasonic diagnosis. An ultrasound probe in which, in order to match the acoustic impedance of the backing layer 27 to the acoustic impedance of the semiconductor substrate, the acoustic impedance was set to 20 MRayl using a composite material of PVC-tungsten and the other components are the same as those in the example 2 is described in FIG. 8 as a comparative example 3.

As it is evident from FIG. 8, the sound pressure reflection coefficient on the interface between the semiconductor substrate 15 and the backing layer 27 is lower at the general working frequency of ultrasound (2 to 15 MHz) in the example 2 in which the acoustic impedance of the backing layer 27 is set close to the acoustic impedance of the acoustic lens 3 than in the comparative example 3 in which the acoustic impedance of the backing layer 27 is matched to the acoustic impedance of the semiconductor substrate 15. For example, when the working frequency of ultrasound was 5 MHz, the sound pressure reflection coefficient was 85% in the comparative example 3. However, in the example 2, the sound pressure reflection coefficient was able to be reduced to 58%.

When the example 1 and the example 2 are compared, the sound pressure reflection coefficient of the interface between the semiconductor substrate 15 and the backing layer 27 is lower in the example 2. Therefore, it is seen that the sound pressure reflection coefficient of the interface between the semiconductor substrate 15 and the backing layer 27 is lower and a suppression effect for multiple reflection is higher when the thickness of the semiconductor substrate 15 is smaller.

In the example 2, as in the example 1, it is possible to suppress a warp amount of the bonded body of the semiconductor substrate 15 and the backing layer 27 to about 10 mm.

EXAMPLE 3

Figure 9:
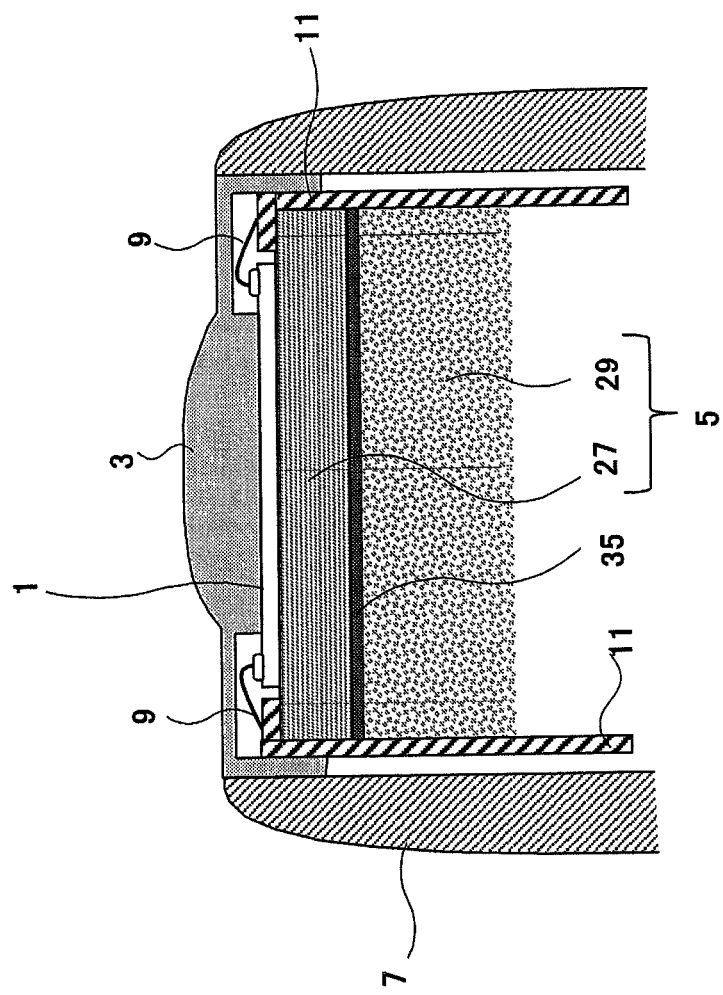
FIG. 9 is a sectional view in the minor axis direction of an ultrasound probe in an example 3.

In FIG. 9, a sectional view in the minor axis direction of an ultrasound probe in an example 3 is shown. The example 3 is different from the example 1 in that the second backing layer 29 is formed of ferrite rubber and the first backing layer 27 and the second backing layer 29 are bonded by an adhesive of thermo-setting epoxy resin. The other components are the same as those in the first embodiment. Therefore, the components are denoted by the same reference numerals and explanation of the components is omitted.

The ferrite rubber is molded in set dimensions or cut and molded in the set dimensions. The ferrite rubber is used for the backing layer 29 as an attenuating material. The backing layer 27 and the backing layer 29 were bonded via an epoxy resin layer 35 of an adhesive material. In this case, the thickness of the epoxy resin layer 35 is reduced to thickness equal to or smaller than 10 µm. Consequently, since material thickness can be markedly reduced compared with the wavelength at the working frequency of ultrasound, the acoustic impedance of the epoxy resin layer 35 can be neglected. Therefore, it is possible to suppress reflection of the ultrasound on an interface of the epoxy resin layer 35.

In the ultrasound probe in the example 3, as in the example 1, the sound pressure reflection coefficient on the interface between the semiconductor substrate 15 and the backing layer 27 was able to be reduced. A warp amount of the joined body of the semiconductor substrate 15 and the backing layer 27 was 5 mm, which is smaller than the warp amount in the example 1.

As the backing layer 29, besides ferrite rubber, a material including a backing material in an ordinary ultrasound probe as a base such as vinyl-chloride vinyl-acetate copolymer resin containing tungsten can be used.

The adhesive material is not limited to the epoxy resin. A material having hardening temperature close to the room temperature and having a low modulus of elasticity can be used.

EXAMPLE 4

An example 4 is explained below. The example 4 is different from the example 1 shown in FIG. 1 in that the thickness of the semiconductor substrate 15 is set to 25 µm. Further, the example 4 is different from the example 1 in that the second backing layer 29 is formed at thickness of 3 mm from a composite material obtained by mixing tungsten and micro balloons in thermosetting epoxy resin. Since the other components are the same as those in the example 1, explanation of the components is omitted.

The backing layer 29 is formed by mixing tungsten and micro balloons, which are hollow particles, in epoxy resin. When the micro balloons are mixed, the attenuation ratio of ultrasound can be increased although the acoustic impedance is the same. Therefore, compared with the example 1, in the example 4, the thickness of the backing layer 29 can be halved.

Figure 10:
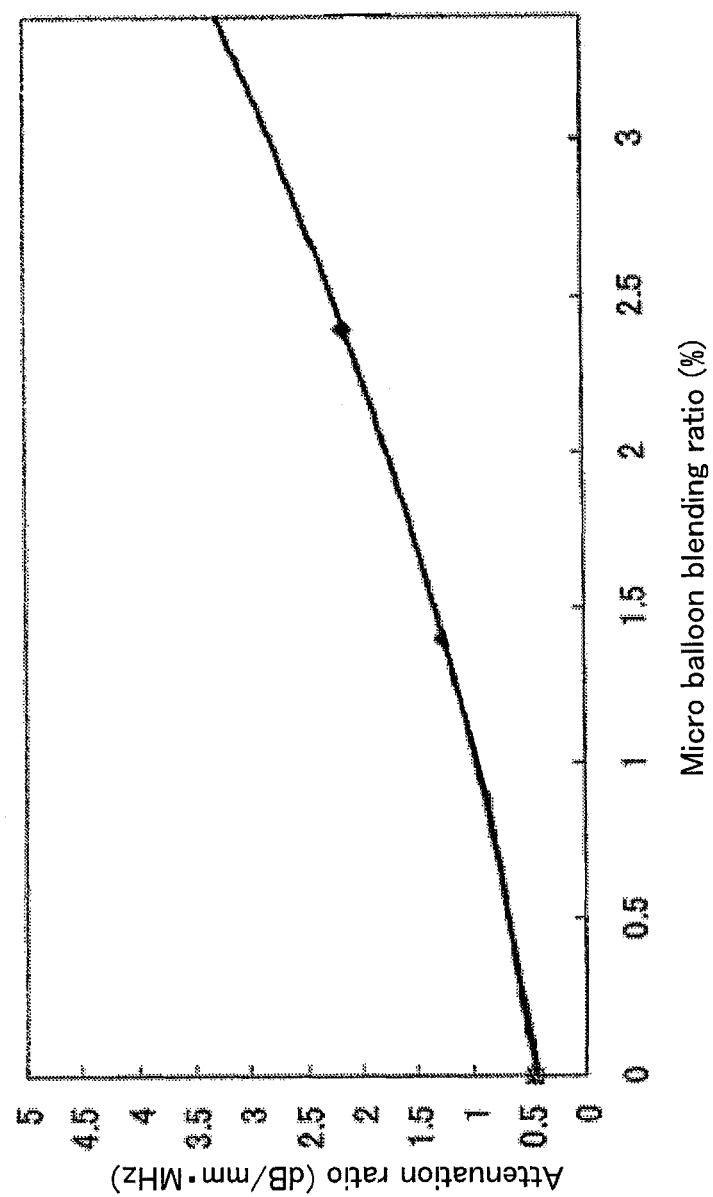
FIG. 10 is a graph showing a relation between the attenuation ratio of ultrasound of a second backing layer and a blending quantity of micro balloons in an example 4.

A relation between the attenuation ratio of ultrasound of the backing layer 29 and the blending quantity of the micro balloons is shown in FIG. 10. FIG. 10 is a graph in which the ordinate indicates the ultrasound attenuation ratio of the backing layer 29 and the abscissa indicates the blending ratio of the micro balloons. As it is evident from the graph in FIG. 10, when the blending quantity of the micro balloons increases, the attenuation ratio of ultrasound increases. Therefore, since the backing layer 29 can be reduced in thickness, the ultrasound probe can be reduced in weight. Note that, in the backing layer 29 in the example 4, an acoustic impedance is set to 4 MRayl, a coefficient of linear expansion is set to 100 ppm/° C., a modulus of elasticity is set to 500 MPa, and a hardening temperature is set to 40° C.

Figure 11:
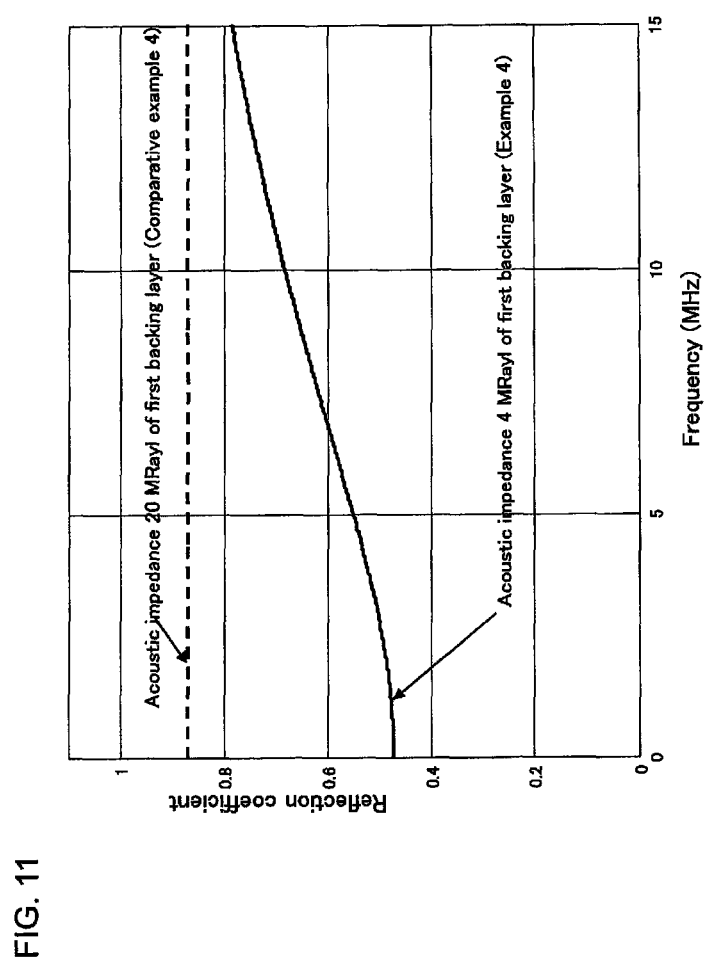
FIG. 11 is a graph showing the sound pressure reflection coefficient of an interface between a semiconductor substrate and a backing layer in the example 4.

In FIG. 11, the sound pressure reflection coefficient of ultrasound on the interface between the semiconductor substrate 15 and the backing layer 27 of an ultrasound probe in the example 4 is shown. FIG. 11 is a graph in which the ordinate indicates the sound pressure reflection coefficient of the interface between the semiconductor substrate 15 and the backing layer 27 and the abscissa indicates the working frequency of ultrasound used for an ultrasonic diagnosis. Note that, for comparison, a sound pressure reflection coefficient in a comparative example 4 in which, in order to match the acoustic impedance of the first backing layer 27 to the acoustic impedance of the semiconductor substrate, the acoustic impedance is set to 20 MRayl using a composite material of PVC-tungsten and the other components are formed the same as those in the example 4 is described in FIG. 11.

As shown in FIG. 11, in the ultrasound probe in the example 4, the sound pressure reflection coefficient on the interface between the semiconductor substrate 15 and the first backing layer 27 was able to be further reduced than in the comparative example 4. For example, the sound pressure reflection coefficient was able to be reduced from 85% to 55% when the working frequency of ultrasound was 5 MHz. The sound pressure reflection coefficient was able to be reduced from 85% to 70% as well when the working frequency of ultrasound was near 10 MHz. A warp amount during bonding of the semiconductor substrate 15 and the first backing layer 27 was able to be reduced to about 5 mm.

EXAMPLE 5

Figure 12:
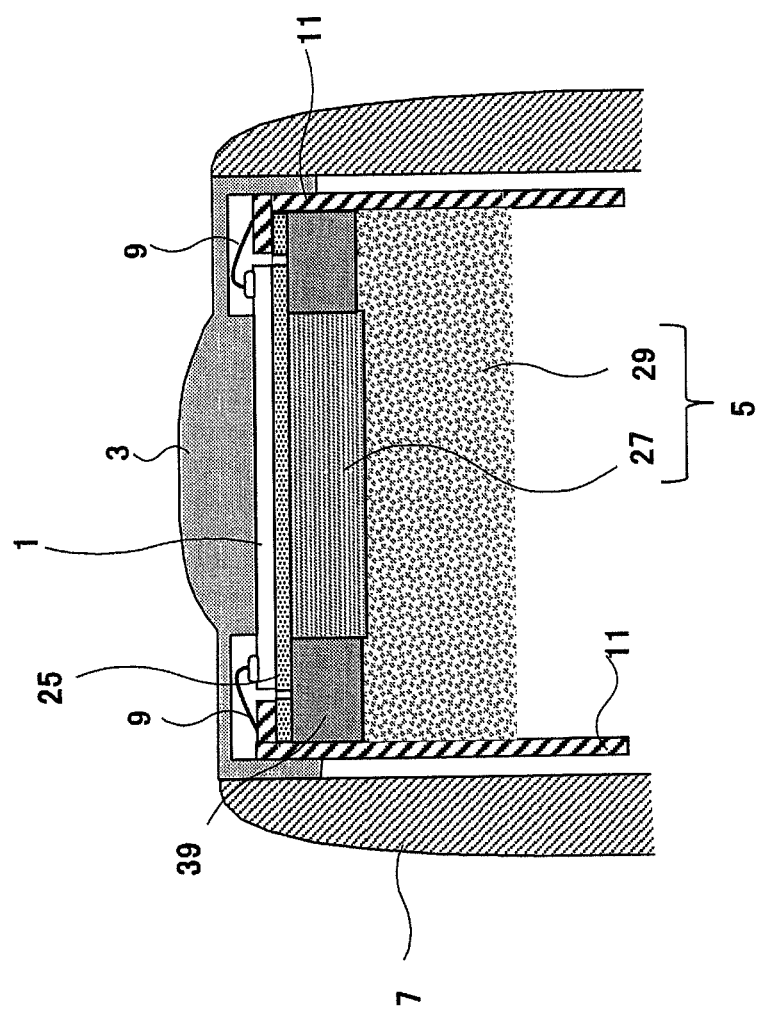
FIG. 12 is a sectional view in the minor axis direction of an ultrasound probe in an example 5.

A sectional structure of an ultrasound probe in an example 5 is shown in FIG. 12. The example 5 is different from the example 1 in that a frame material 39 is bonded to the rear face side of the semiconductor substrate 15 via the adhesive layer 25. The example 5 is different from the example 1 in that the center portion of the frame material 39 is bored and the first backing layer 27 is inserted into the bored portion and bonded to the rear face side of the semiconductor substrate 15 via the adhesive layer 25. Since the other components are the same as those in the example 1, the components are denoted by the same reference numerals and explanation of the components is omitted.

The frame material 39 is formed of a material such as ceramic or an alloy and plays a role of a base for fixing the CMUT chip 1 and the flexible substrate 11. The bored portion into which the backing layer 27 can be inserted is formed in the center portion of the frame material 39. The backing layer 27 is inserted into the bored portion and fixed. The backing layer 27 is formed smaller than the CMUT chip 1. Since an acoustic radiation section (an ultrasound radiating section) of the CMUT chip 1 is not present over the entire CMUT chip 1, the backing layer 27 is arranged only in the center portion where the acoustic radiation section is present. The acoustic radiation section is covered by the backing layer 27.

Consequently, since the CMUT chip 1 can be supported by the frame material 39, the structure of which is more stable than the backing layer 27, it is possible to improve practical utility of assembly work and the like for the ultrasound probe. A suppression effect for multiple reflection and a reduction effect for structural distortion in the example 5 is the same as those in the example 1.

EXAMPLE 6

An ultrasound probe in an example 6 is explained below. The example 6 is different from the example 1 shown in FIG. 1 in that resin is filled in porous ceramic to form the first backing layer 27. The example 6 is different from the example 1 in that tungsten is mixed in thermosetting epoxy resin to form the second backing layer 29. Since the other components are the same as those in the example 1, explanation of the components is omitted.

In the backing layer 27, an acoustic impedance was set to 6 MRayl and a coefficient of linear expansion was set to 10 ppm/° C. In the backing layer 29, an acoustic impedance was set to 6 MRayl, a coefficient of linear expansion was set to 80 ppm/° C., a modulus of elasticity was set to 500 MPa, and thickness was set to 6 mm. The backing layer 29 was formed by the pouring at hardening temperature of 40° C. as in the example 1. Note that the thickness of the semiconductor substrate 15 was set to 40 μm.

Figure 13:
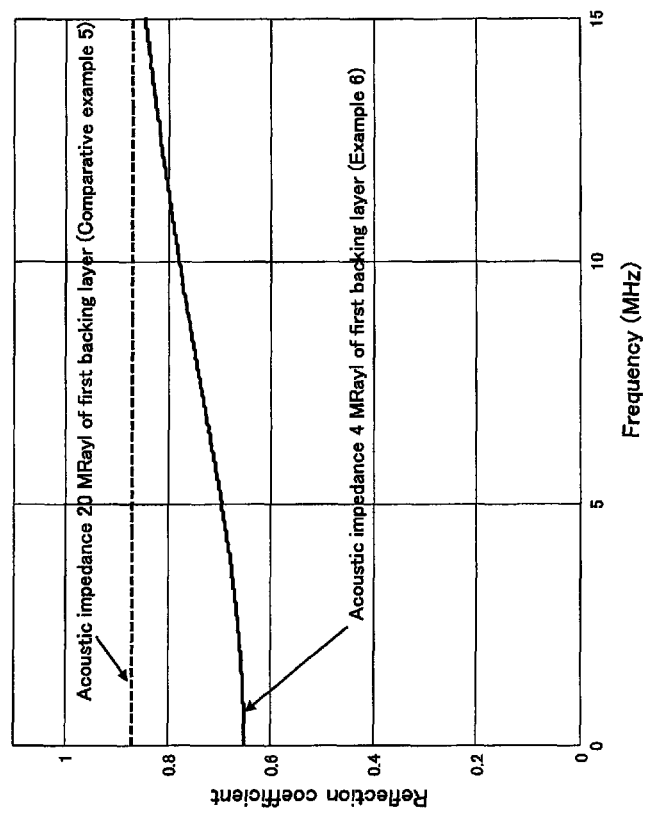
FIG. 13 is a graph showing the sound pressure reflection coefficient of an interface between a semiconductor substrate and a backing layer in an example 6.

In FIG. 13, the sound pressure reflection coefficient of ultrasound on the interface between the semiconductor substrate 15 and the backing layer 27 of the ultrasound probe in the example 6 is shown. FIG. 13 is a graph in which the ordinate indicates the sound pressure reflection coefficient of the interface between the semiconductor substrate 15 and the backing layer 27 and the abscissa indicates the working frequency of ultrasound used for an ultrasonic diagnosis. Note that, for comparison, a sound pressure reflection coefficient in a comparative example 5 in which, in order to match the acoustic impedance of the first backing layer 27 to the acoustic impedance of the semiconductor substrate, the acoustic impedance is set to 20 MRayl using a composite material of PVC-tungsten and the other components are formed the same as those in the example 6 is described in FIG. 13.

As shown in FIG. 13, in the ultrasound probe in the example 6, the sound pressure reflection coefficient on the interface between the semiconductor substrate 15 and the first backing layer 27 was able to be further reduced than in the comparative example 5. For example, the sound pressure reflection coefficient was able to be reduced from 85% to 70% when the working frequency of ultrasound is 5 MHz. On the other hand, since the acoustic impedance was larger in the example 6 than in the example 1, the sound pressure reflection coefficient was larger in the example 6 than in the example 1. Therefore, when the sound pressure reflection coefficient on the interface between the semiconductor substrate 15 and the backing layer 27 is set lower than, for example, 85%, it is desirable to set the acoustic impedance of the backing layer 27 to an acoustic impedance equal to or lower than 6 MRayl.

Reference Sings List
1 CMUT chip
3 Acoustic lens
5 Backing layer
13 CMUT cell
15 Semiconductor substrate
27 First backing layer
29 Second backing layer
33 Carbon fiber

The invention claimed is:

1. An ultrasound probe comprising:
a capacitive vibration element configured to mutually convert ultrasound and an electric signal;
a semiconductor substrate including a plurality of the capacitive vibration elements formed on the surface thereof;
an acoustic lens provided on a front face side of the capacitive vibration element; and
a backing layer provided on a rear face side of the semiconductor substrate,
wherein the backing layer includes a first backing layer set in contact with the semiconductor substrate and a second backing layer provided on a rear face side of the first backing layer,
wherein an acoustic impedance of the first backing layer is set on the basis of a thickness of the semiconductor substrate,
wherein the second backing layer is formed of an attenuating material capable of attenuating the ultrasound transmitted through the first backing layer, and
wherein an acoustic impedance of the second backing layer is set to match the acoustic impedance of the first backing layer.

2. The ultrasound probe according to claim 1, wherein the acoustic impedance of the first backing layer is set to a value close to an acoustic impedance of the acoustic lens compared with an acoustic impedance of the semiconductor substrate.

3. The ultrasound probe according to claim 1, wherein the first backing layer is formed of resin and is formed by mixing, in the resin, an adjusting material for adjusting a coefficient of linear expansion of the first backing layer to be close to a coefficient of linear expansion of the semiconductor substrate.

4. The ultrasound probe according to claim 3, wherein the adjusting material is carbon fiber or glass fiber and is mixed in the resin with a longitudinal direction of the fiber adjusted to a longitudinal direction of the first backing layer.

5. The ultrasound probe according to claim 1, wherein the first backing layer is formed by filing resin in porous ceramic.

6. The ultrasound probe according to claim 3, wherein an ultrasound attenuation ratio of the second backing layer is higher than an ultrasound attenuation ratio of the first backing layer.

7. The ultrasound probe according to claim 6, wherein the second backing layer is formed using resin having a modulus of elasticity smaller than that of the resin used for the first backing layer.

8. The ultrasound probe according to claim 7, wherein the acoustic impedance of the second backing layer is set close to the acoustic impedance of the first backing layer by mixing tungsten or silicon in the resin forming the second backing layer.

9. The ultrasound probe according to claim 3, wherein the thickness of the semiconductor substrate is equal to or larger than 25 μm and equal to or smaller than 50 μm.

10. The ultrasound probe according to claim 3,
wherein a frequency range of the ultrasound is equal to or higher than 2 MHz and equal to or lower than 15 MHz, and
wherein the acoustic impedance of the first backing layer is set to an acoustic impedance equal to or larger than 1.5 MRayl and equal to or smaller than 6 MRayl and, desirably, equal to or larger than 4 MRayl and equal to or smaller than 6 MRayl.

11. An ultrasound probe comprising:
a capacitive vibration element configured to mutually convert ultrasound and an electric signal;
a semiconductor substrate including a plurality of the capacitive vibration elements formed on the surface thereof;
an acoustic lens provided on a front face side of the capacitive vibration element; and
a backing layer provided on a rear face side of the semiconductor substrate,
wherein the backing layer includes a first backing layer set in contact with the semiconductor substrate and a second backing layer provided on a rear face side of the first backing layer,
wherein an acoustic impedance of the second backing layer is set to match the acoustic impedance of the first backing layer,
wherein the first backing layer is formed to resin and is formed by mixing, in the resin, an adjusting material for adjusting a coefficient of linear expansion of the first backing layer to be close to a coefficient of linear expansion of the semiconductor substrate, and
wherein the adjusting material is carbon fiber or glass fiber is mixed in the resin with a longitudinal direction of the fiber adjusted to a longitudinal direction of the first backing layer.

12. An ultrasound probe comprising:
a capacitive vibration element configured to mutually convert ultrasound and an electric signal;
a semiconductor substrate including a plurality of the capacitive vibration elements formed on the surface thereof;
an acoustic lens provided on a front face side of the capacitive vibration element; and
a backing layer provided on a rear face side of the semiconductor substrate,
wherein the backing layer includes a first backing layer set in contact with the semiconductor substrate and a second backing layer provided on a rear face side of the first backing layer,
wherein an acoustic impedance of the first backing layer is set based on thickness of the semiconductor substrate,
wherein the second backing layer is formed of an attenuating material capable of attenuating the ultrasound transmitted through the first backing layer,
wherein an acoustic impedance of the second backing layer is set to match the acoustic impedance of the first backing layer, and
wherein the thickness of the semiconductor substrate is equal to or larger than 25 mm and equal to or smaller than 50 mm.

* * * * *